(12) United States Patent
Elmén

(10) Patent No.: US 9,833,578 B2
(45) Date of Patent: Dec. 5, 2017

(54) MEDICAMENT DELIVERY DEVICE

(71) Applicant: Carebay Europe Ltd, Swatar (MT)

(72) Inventor: Gunnar Elmén, Huddinge (SE)

(73) Assignee: Carebay Europe Ltd, Sliema (MT)

( * ) Notice: Subject to any disclaimer, the term of this patent is extended or adjusted under 35 U.S.C. 154(b) by 149 days.

(21) Appl. No.: 14/434,971

(22) PCT Filed: Oct. 8, 2013

(86) PCT No.: PCT/EP2013/070885
§ 371 (c)(1),
(2) Date: Apr. 10, 2015

(87) PCT Pub. No.: WO2014/056874
PCT Pub. Date: Apr. 17, 2014

(65) Prior Publication Data
US 2015/0250953 A1    Sep. 10, 2015

Related U.S. Application Data

(60) Provisional application No. 61/712,961, filed on Oct. 12, 2012.

(30) Foreign Application Priority Data

Oct. 12, 2012  (SE) ...................................... 1251158

(51) Int. Cl.
*A61M 5/19*     (2006.01)
*A61M 5/315*    (2006.01)
(Continued)

(52) U.S. Cl.
CPC .......... *A61M 5/31596* (2013.01); *A61M 5/19* (2013.01); *A61M 5/2033* (2013.01);
(Continued)

(58) Field of Classification Search
CPC .. A61M 5/31596; A61M 5/19; A61M 5/2066; A61M 5/2448; A61M 5/31571;
(Continued)

(56) References Cited

U.S. PATENT DOCUMENTS 4,755,169 A   7/1988 Sarnoff et al.
6,319,225 B1  11/2001 Sugita et al.
(Continued)

FOREIGN PATENT DOCUMENTS

SE  WO 2012067584 A1 *  5/2012  .............. A61M 5/19
WO     2004/004809 A1    1/2004
(Continued)

OTHER PUBLICATIONS

EPO, Int'l Search Report in PCT/EP2013/070885, dated Jan. 20, 2014.
EPO, Written Opinion in PCT/EP2013/070885, dated Jan. 20, 2014.

*Primary Examiner* — Nathan R Price
*Assistant Examiner* — Courtney Fredrickson
(74) *Attorney, Agent, or Firm* — Piedmont Intellectual Property

(57) ABSTRACT

A medicament delivery device includes a distal housing part; a proximal housing part for a container; a drive mechanism in the distal housing part that includes a plunger rod; and an auto mixing mechanism. The housing parts are movable from a first position, in which the housing parts are partially extended relative to each other, to a second position, in which the housing parts are partially retracted relative to each other. The auto mixing mechanism is configured to hold the housing parts in the first position and to lock the housing parts in the second position, and includes a mixing force member operably arranged between the housing parts such that manual activation of the auto mixing mechanism enables the mixing force member to cause the housing parts (Continued)

Figure 1:
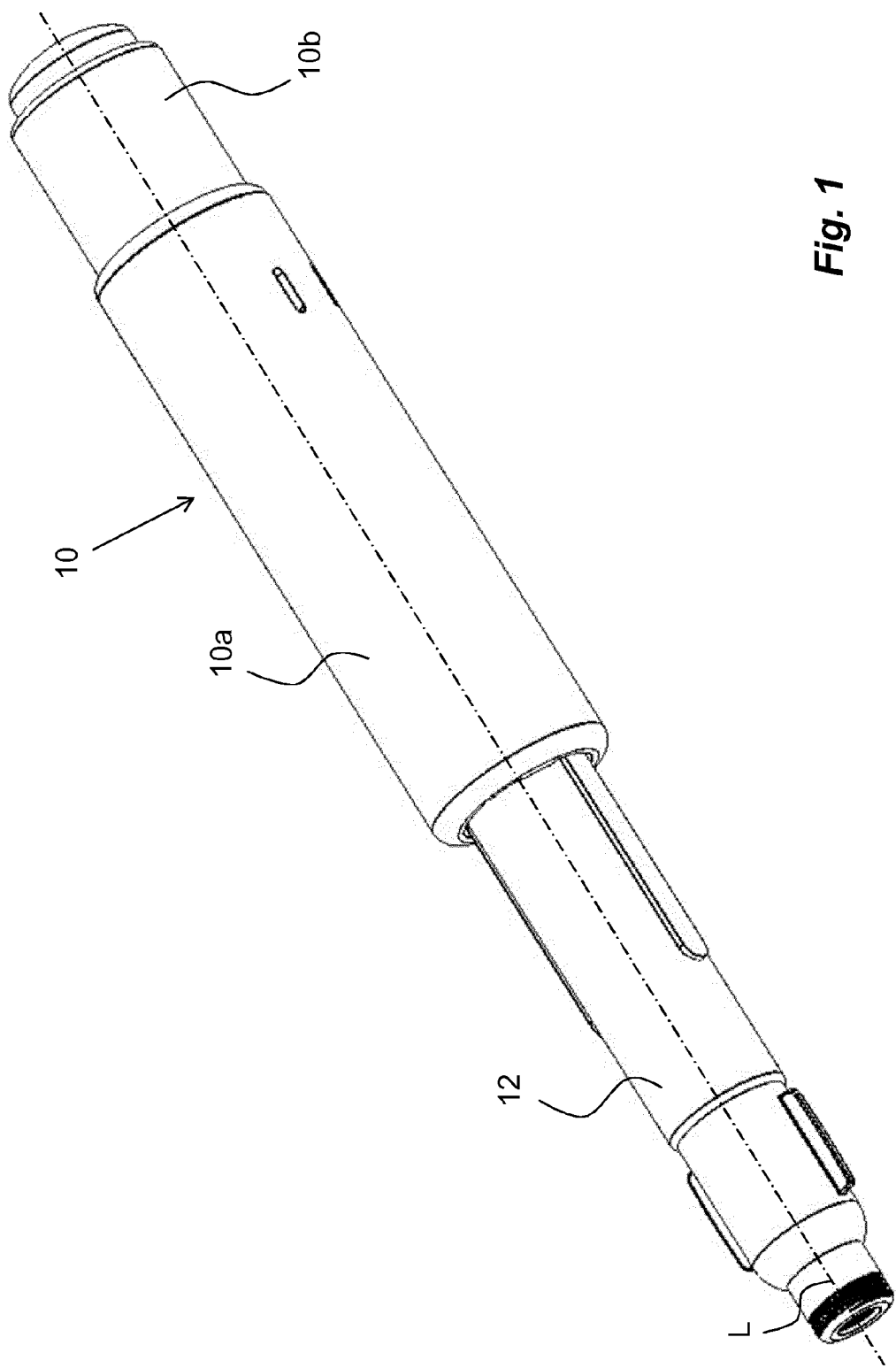

to move from the first position to the second position. The plunger rod acts to mixing a medicament in the container.

12 Claims, 13 Drawing Sheets

(51) Int. Cl.
*A61M 5/28* (2006.01)
*A61M 5/20* (2006.01)
*A61M 5/24* (2006.01)

(52) U.S. Cl.
CPC ........ *A61M 5/2066* (2013.01); *A61M 5/2448* (2013.01); *A61M 5/284* (2013.01); *A61M 5/3158* (2013.01); *A61M 5/31571* (2013.01); *A61M 2005/2485* (2013.01); *A61M 2005/2492* (2013.01); *A61M 2205/581* (2013.01); *A61M 2205/582* (2013.01); *F04C 2270/0421* (2013.01)

(58) Field of Classification Search
CPC ........ A61M 5/3158; A61M 2005/2485; A61M 5/284; A61M 5/2451
See application file for complete search history.

(56) References Cited

U.S. PATENT DOCUMENTS

| | | | |
|---|---|---|---|
| 6,793,646 | B1 | 9/2004 | Giambattista et al. |
| 2005/0049550 | A1* | 3/2005 | Kirchhofer ......... A61M 5/2448 604/82 |
| 2005/0209569 | A1 | 9/2005 | Ishikawa et al. |

FOREIGN PATENT DOCUMENTS

| | | |
|---|---|---|
| WO | 2009/147026 A1 | 12/2009 |
| WO | 2010/081489 A1 | 7/2010 |
| WO | 2010/085903 A1 | 8/2010 |
| WO | 2011/099918 A1 | 8/2011 |

* cited by examiner

MEDICAMENT DELIVERY DEVICE

TECHNICAL FIELD

The present invention relates to a medicament delivery device for administering, dispensing or delivering medicaments in a safe and reliable way. More particularly, it relates to a medicament delivery device for manually penetrating the skin of a patient using a needle arranged to said device and to automatically injecting a drug mixture from a multiple-chamber container.

BACKGROUND ART

There are types of medicaments that can be stored for a long time and that are filled in containers, such as cartridges, syringes, ampoules, canisters or the like, containing a ready-to-use medicament in liquid state. However, there are also other types of medicaments that are a mixture of two substances, i.e. a medicament agent (e.g. lyophilized, powdered or concentrated liquid) and a diluent (e.g. water, dextrox solution or saline solution). These types of medicaments cannot be pre-mixed and stored for a long time because the medicament agent is unstable and can be degraded and lose its effect quickly. Hence, a user, e.g. a patient himself/herself, a physician, a nurse, hospital personnel or trained persons, must perform the mixing within a limited time period prior to delivery of a dose of medicament to a patient. Further, some medicament agents are subject to chemical changes during mixing. Such sensitive medicament agents require a particular treatment when mixing with a diluent, since excessive mixing force will degrade said medicament agents.

In order to facilitate the mixing, a number of containers for mixing have been developed to comprise at least two chambers, known as multi-chamber containers. These multi-chambered containers comprise a first chamber containing the medicament agent and at least a second chamber containing the diluent. These chambers are sealed off with stoppers such/so that the medicament agents are separated from the diluent and do not become degraded. When the medicament agent is to be mixed, shortly before administering, redirecting passages are opened between the chambers, usually by depressing a distal stopper and in turn a divider stopper of the container somewhat. The passages allow the mixing of the medicament agent and the diluent to prepare the medicament for delivery.

The above mentioned requirements can be achieved by simple medicament delivery devices, such as a common hypodermic syringe, but the procedure is of course rather awkward, in particular for users who are not used to handle these devices. In order to facilitate for the patient to self-administer the medicament with a predetermined dose in an easy, safe and reliable way and also to facilitate the administration of medicaments for hospital personnel in the same facilitated way, a number of automatic and semi-automatic devices have been developed, incorporating these multiple-chamber solutions, to mix the medicament before delivery.

A self-injection device arranged with a dual-chamber container, wherein both the mixing and the injection are done automatically by mechanical means, such as springs and other means, is disclosed in U.S. Pat. No. 4,755,169. A similar solution is disclosed in U.S. Pat. No. 6,793,646 wherein the mixing of a dual-chamber cartridge is done automatically by springs upon activation of the device. The injection is done automatically by applying a forwardly-directed force to a plunger rod using the same spring as used for the mixing action. A drawback with these devices is that the mixing force, which medicament agents are subjected to, is initially very high, as described by Hooke's law. Hence, the medicament agents may be degraded.

Another solution is disclosed in WO 2004004809, wherein both the mixing and the injection are done automatically by electronically controlled means. A drawback with this device is that the electronics are dependent on batteries and are very sensitive to noise, moisture, water, etc., which can result in device malfunction. Furthermore, the manufacture of electronic devices is more expensive than the manufacture of mechanical devices.

In U.S. Pat. No. 6,319,225 the mixing of a dual-chamber ampoule is done manually. The device is pushed vertically against a surface, with its proximal end pointing upwards, causing a relative upward movement of a plunger rod and a stopper inside an ampoule, such that mixing is performed. The process is visually observable. U.S. Pat. No. 6,319,225 teaches that the most suitable process for mixing a medicament agent with a diluent, is by manually controlling the speed of the diluent flow under visual inspection. A drawback of this device is that the mixing force, which medicament agents are subjected to, can be high if the user is stressed and urgently needs to use the device. Hence, the medicament agents may be degraded.

Moreover, the handling and safety aspects of injector devices, having a certain degree of automatic functions, as well as providing immediate accessibility in emergency situations, are issues that attract a lot of attention in development of these types of devices.

Even though many of the devices on the market, as well as the ones described above, have their respective advantages, there is still room for improvements, especially improvements regarding the mixing of medicament in a safe and automatic way using components and functions that are dedicated to a mixing sequence.

DISCLOSURE OF INVENTION

In the present application, when the term "distal part/end" is used, this refers to the part/end of the delivery device, or the parts/ends of the members thereof, which is/are located the furthest away from the medicament delivery site of the patient. Correspondingly, when the term "proximal part/end" is used, this refers to the part/end of the delivery device, or the parts/ends of the members thereof, which, is/are located closest to the medicament delivery site of the patient.

The aim of the invention is to provide a medicament delivery device which is uncomplicated and easy to use, which is safe to handle before, during and after use and which displays a high degree of functionality regarding the mixing of medicaments in multi-chamber containers.

This invention is obtained by a medicament delivery device according to the features of claim 1. Preferable embodiments of the invention form the subject of the dependent patent claims.

According to a main aspect of the invention it relates to a medicament delivery device comprising a distal housing part and a proximal housing part. It is to be understood that there may be further housing parts comprised in the device and/or that a housing part may comprise a number of sub-parts.

According to a preferable embodiment, said proximal housing part is arranged to accommodate a multi-compartment medicament container. It is thus to be understood that the medicament container is arranged with at least two compartments that are sealed off initially but when activated are brought into communication with each other for performing a mixing of medicament and diluent.

According to the present invention, said housing parts are designed and arranged to be movable in relation to each other in a longitudinal direction of the medicament delivery device from a first position in which said housing parts are partially extended in relation to each other, to a second position in which said housing parts are partially retracted in relation to each other. The device further comprises a drive mechanism arranged in said distal housing part and comprising a plunger rod. Said plunger rod having a proximally directed end, which may be brought in contact with, and act on, the medicament container.

According to a preferable solution of the invention, it further comprises an auto mixing mechanism configured to hold said housing parts in the first position and to lock said housing parts in the second position wherein said auto mixing mechanism comprises a mixing force member operably arranged between said housing parts, such that manual activation of said auto mixing mechanism allows said mixing force member to cause the two housing parts to move from the first position to the second position whereby said plunger rod acts on said multi-chamber medicament container to perform a mixing of a medicament contained in said multi-compartment medicament container.

According to one aspect of the invention, the mixing force member may comprise a number of different force-providing members. They may include compression springs, gas springs, elastic members, just to mention a few that are within the scope of the skilled person. The mixing force member may be operably arranged between said housing parts and arranged in a tensioned state when the housing parts are in said first position. In this manner, the mixing force member is ready from the beginning such that no measures need to be made by a user before initiating the mixing.

According to another aspect of the invention, the auto mixing mechanism comprises mechanical inter-locking members interacting between the two housing parts and configured to releasably hold said housings in the first position against the tension force exerted by the mixing force member and to lock said housing parts in the second position.

According to a further aspect of the invention, the mechanical inter-locking members are arranged such that said manual activation of said auto mixing mechanism consists of a relative movement of said housing parts for releasing said mixing force member from the tensioned state. More particularly, relative movement of said housing parts is in a non-longitudinal direction of said device. Thus, when a user is to initiate a mixing of medicament, preferably the housing parts are operated manually by the user, wherein the mechanical inter-locking members allow said mixing force member to cause the two housing parts to the second position such that said plunger rod acts on said multi-chamber medicament container for performing a mixing of medicament. The mixing action brings the medicament container towards the plunger rod such that the plunger rod acts on the medicament container, and preferably on a distal stopper of the multi-chamber medicament container such that a mixing is performed.

According to one preferable embodiment of the invention, said mechanical inter-locking members comprise at least one first ledge on a surface of one housing part and at least one first protrusion on a surface of the other housing part. According to one possible solution, the at least one first ledge comprises a seat, into which seat said at least one first protrusion fits, such that when said and at least one first protrusion is positioned in said seat, the housing parts are releasably held in the first position.

According to yet another aspect of the invention, the mechanical inter-locking members further comprise at least one second protrusion on a surface of one housing part and at least one generally wedge-shaped protrusion or resilient tongue on a surface of the other housing part, such that when said at least one second protrusion interacts with said at least one generally wedge-shaped protrusion or resilient tongue, the housing parts are locked in the second position. In this manner the housing parts are locked to each other after a completed mixing, and the subsequent medicament delivery operation can be started.

According to a preferable design of the medicament delivery device, said housing parts may be generally tubular and arranged such that one housing part may move inside said other housing part. This design facilitates the mixing function.

According to a further aspect of the invention, the drive mechanism further comprises a push button protruding from said distal housing part and being interactively connected to the plunger rod; an activation member comprising tubular flexible locking means releasably connected to said plunger rod; drive force means pre-tensioned arranged between a distal end surface of the activation member and a proximal end wall of the plunger rod; a locking member coaxially arranged around said activation member and being distally slidable in relation to said activation member by said proximal housing between a holding position wherein said locking member completely surrounds said tubular flexible locking means holding said plunger rod and thereby said drive force means in a pre-tensioned state and a releasing position wherein said locking member partially surrounds said flexible locking means. The use of a push button and its position on the device provides a positive and intuitive handling of the device during the medicament delivery sequence.

According to another aspect of the invention, the activation member further comprises flexible hook means arranged to interact with annular holding means arranged on the inner circumferential surface of the distal housing part for preventing said push button to be proximally displaced before said locking member is moved from the holding position to the releasing position in order to avoid premature activation of the device.

According to yet another aspect of the invention, the locking member comprises at least two distally extending tongues arranged to come into contact with the flexible hook means when the locking member is displaced from the holding position to the releasing position, whereby the flexible hook means are moved inwards and are free to by-pass the annular holding means.

According to a further aspect of the invention, the push button comprises at least two first proximally extending tongues, and wherein each tongue has a proximally directed surface abutting a distal annular surface of the plunger rod. Also, the tubular flexible locking means comprises generally radial inwardly directed ledges and that said plunger rod comprises a circumferential groove shaped for the ledges to fit into said groove.

According to another aspect of the invention, the device is an injection device, preferably an auto-injector.

These and other aspects of and advantages with the present invention will become apparent from the following detailed description and from the accompanying drawings.

BRIEF DESCRIPTION OF FIGURES IN THE DRAWINGS

Figure 2:
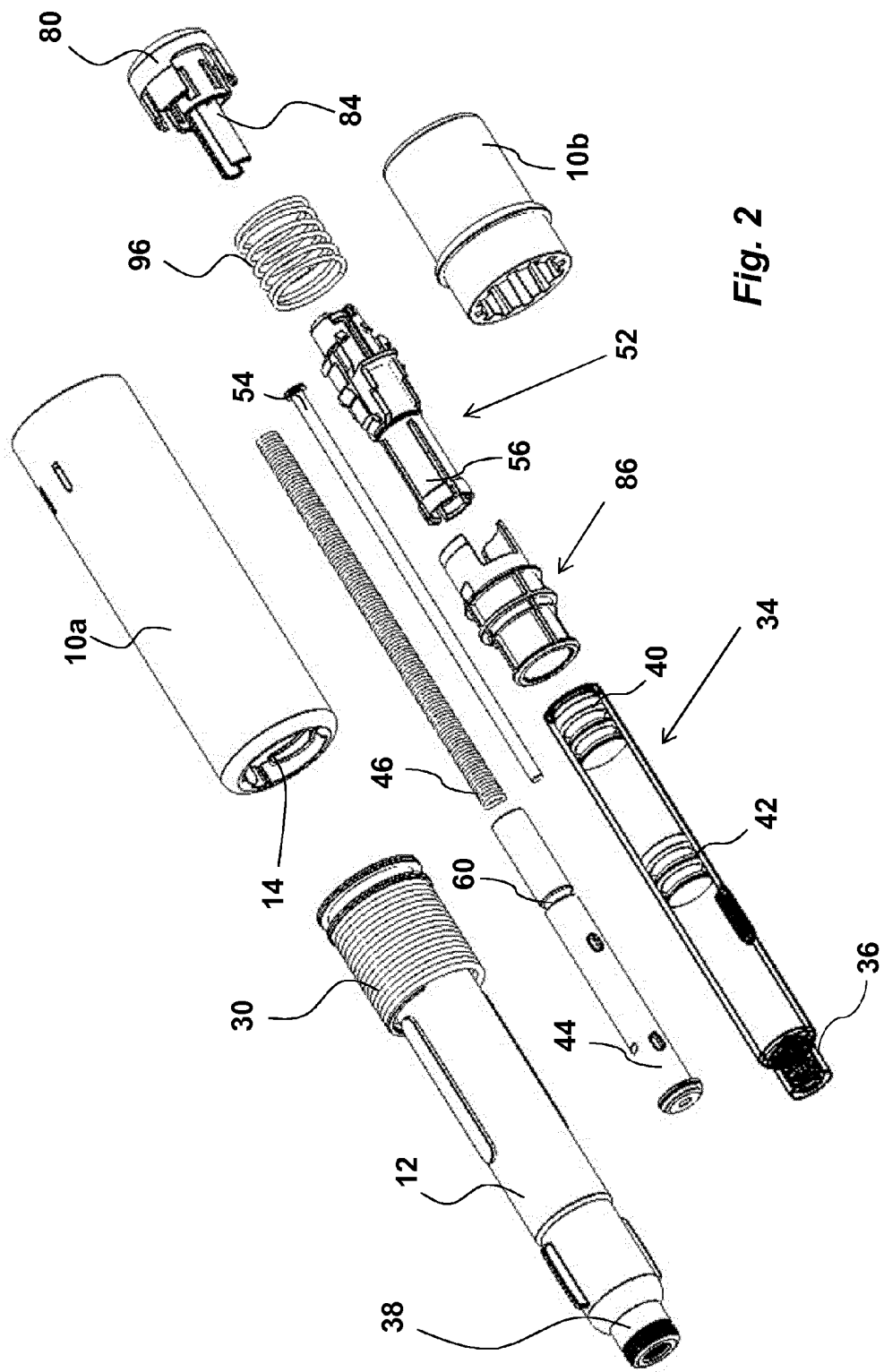
Figure 3:
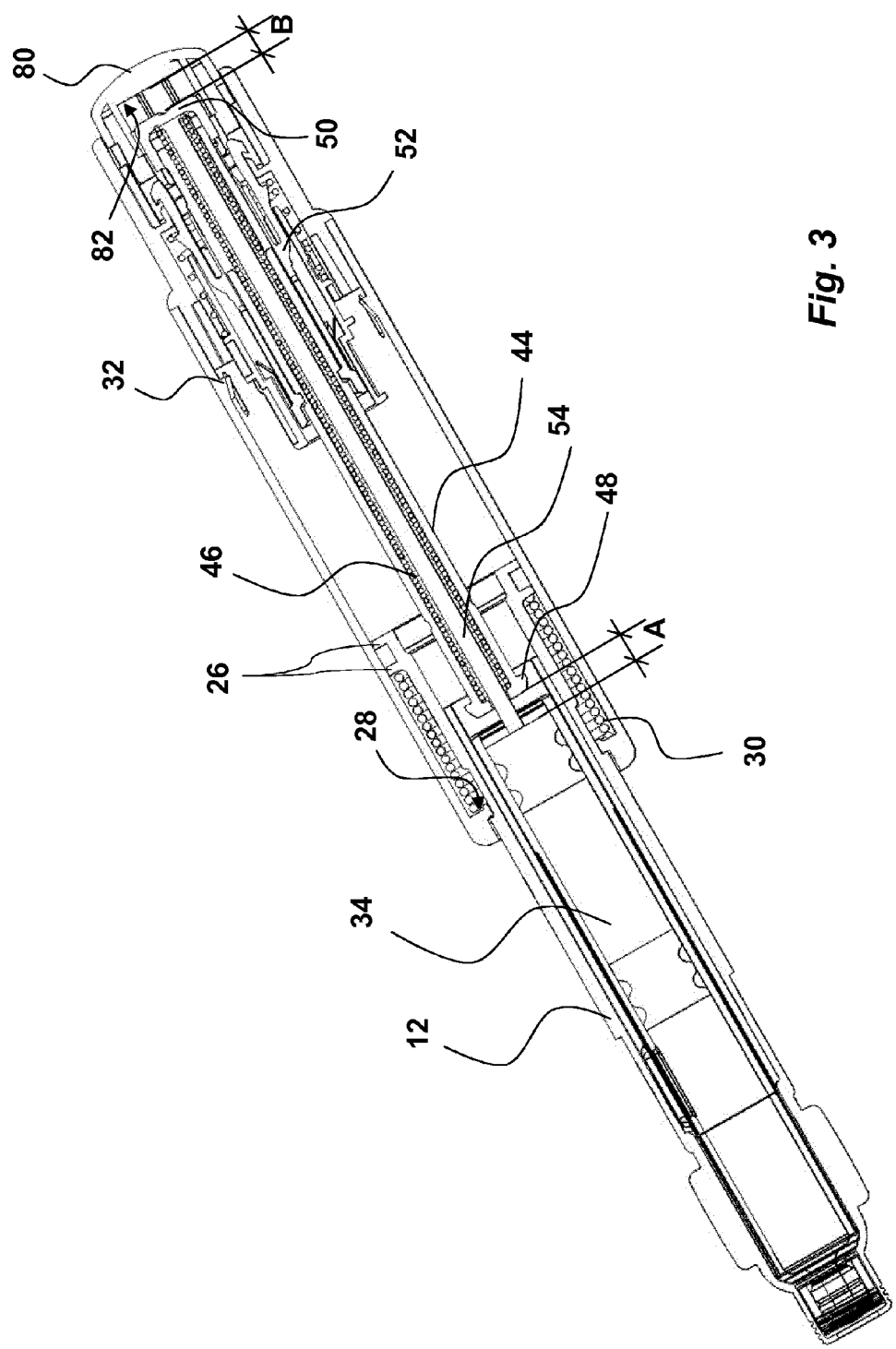
Figure 8:
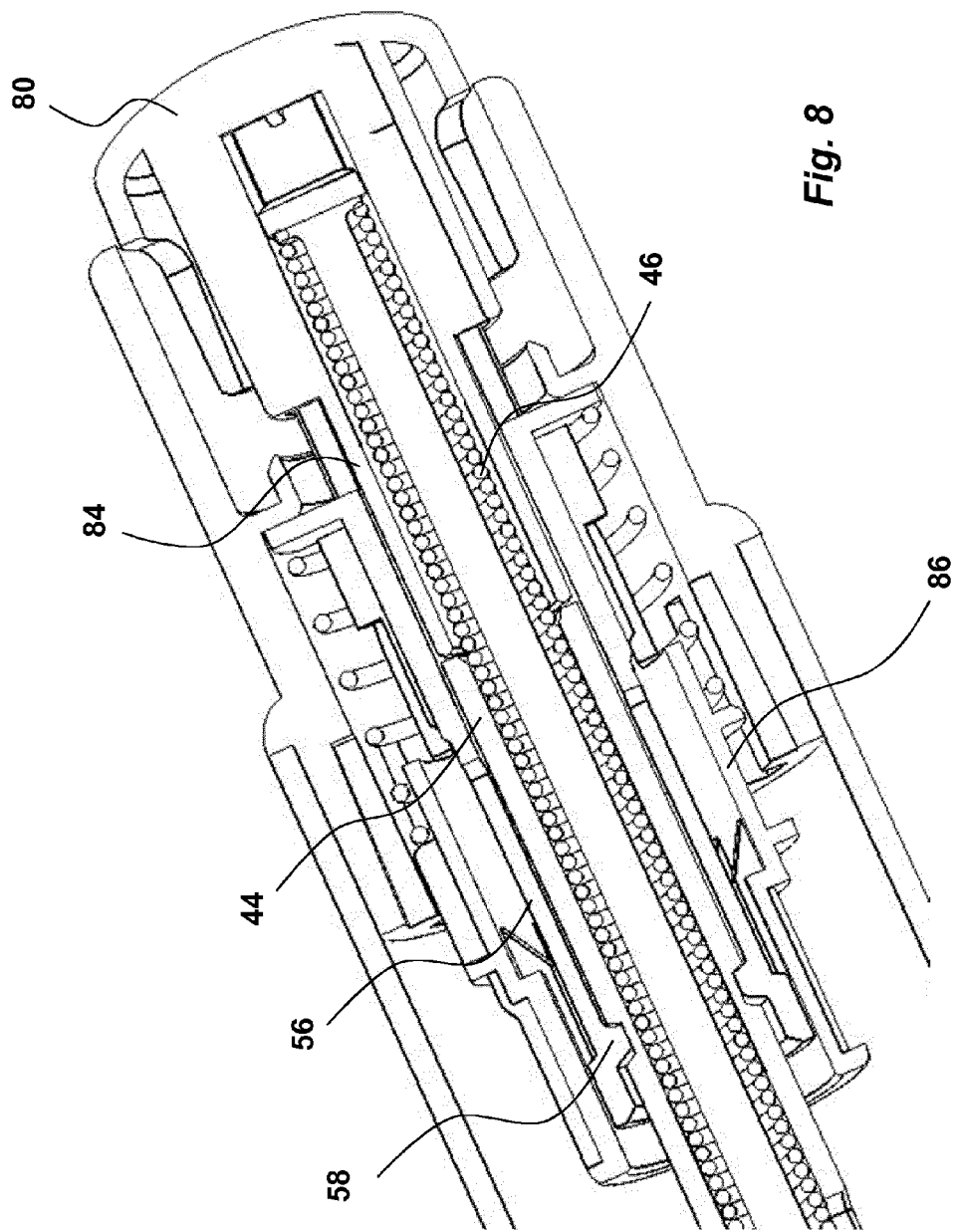
Figure 9:
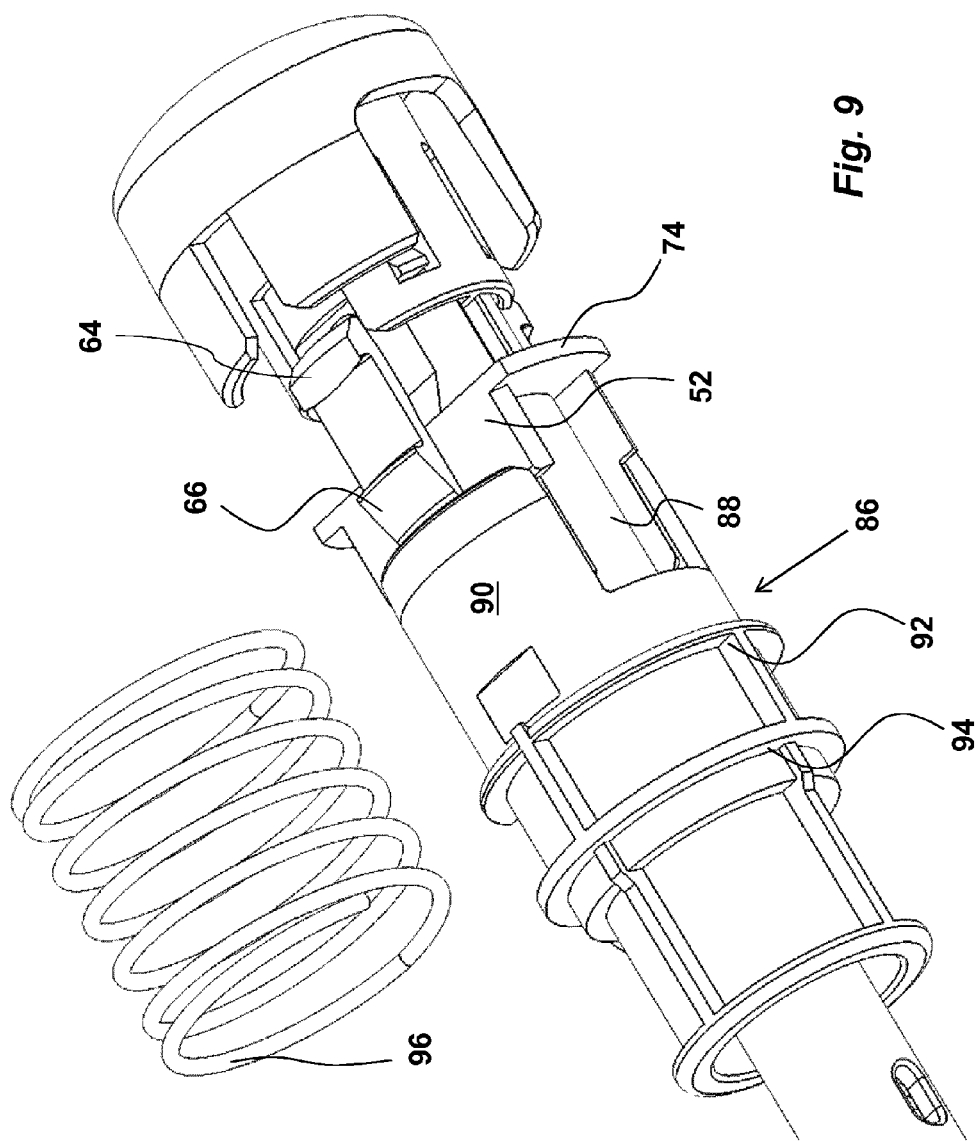
Figure 10:
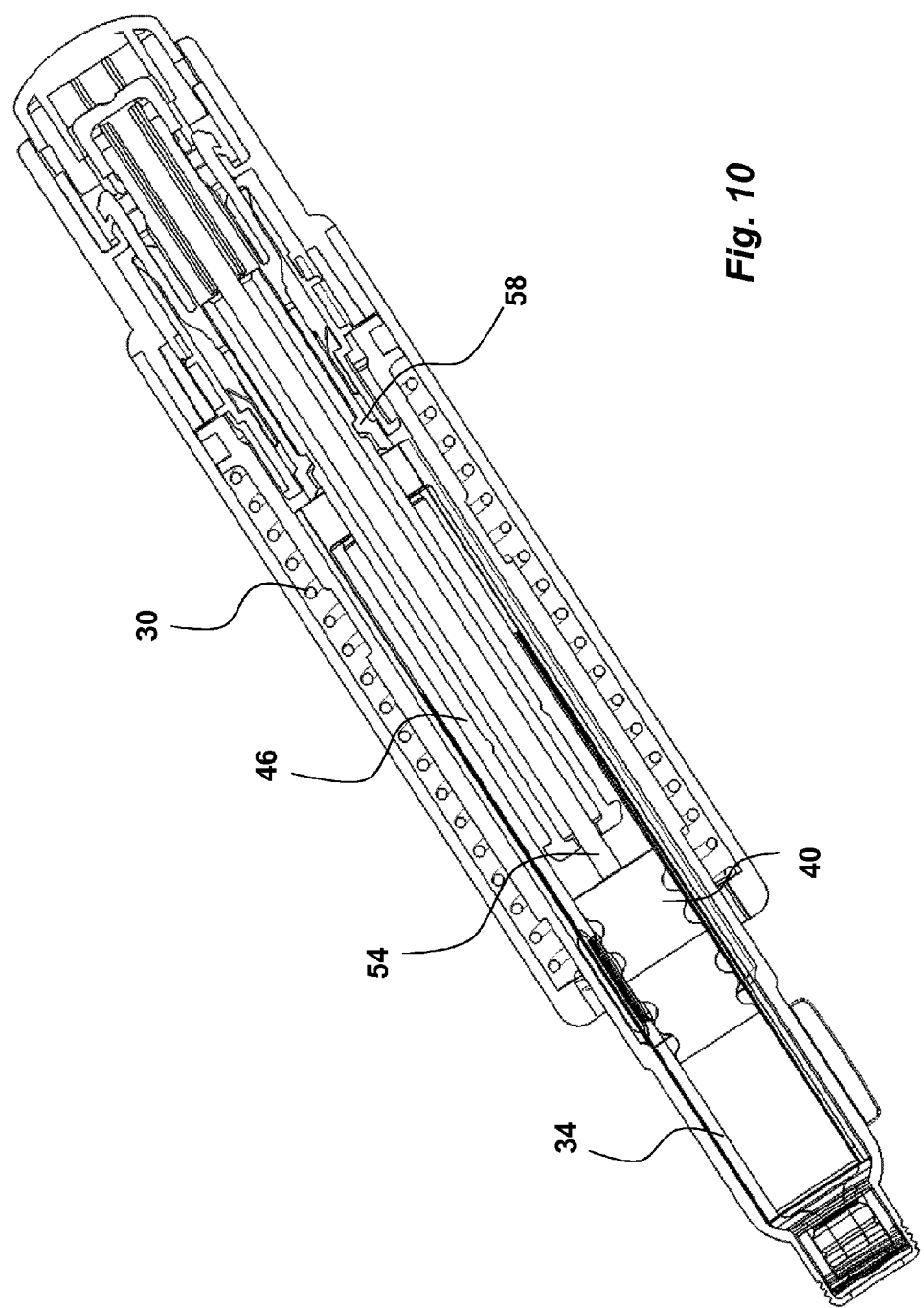
Figure 11:
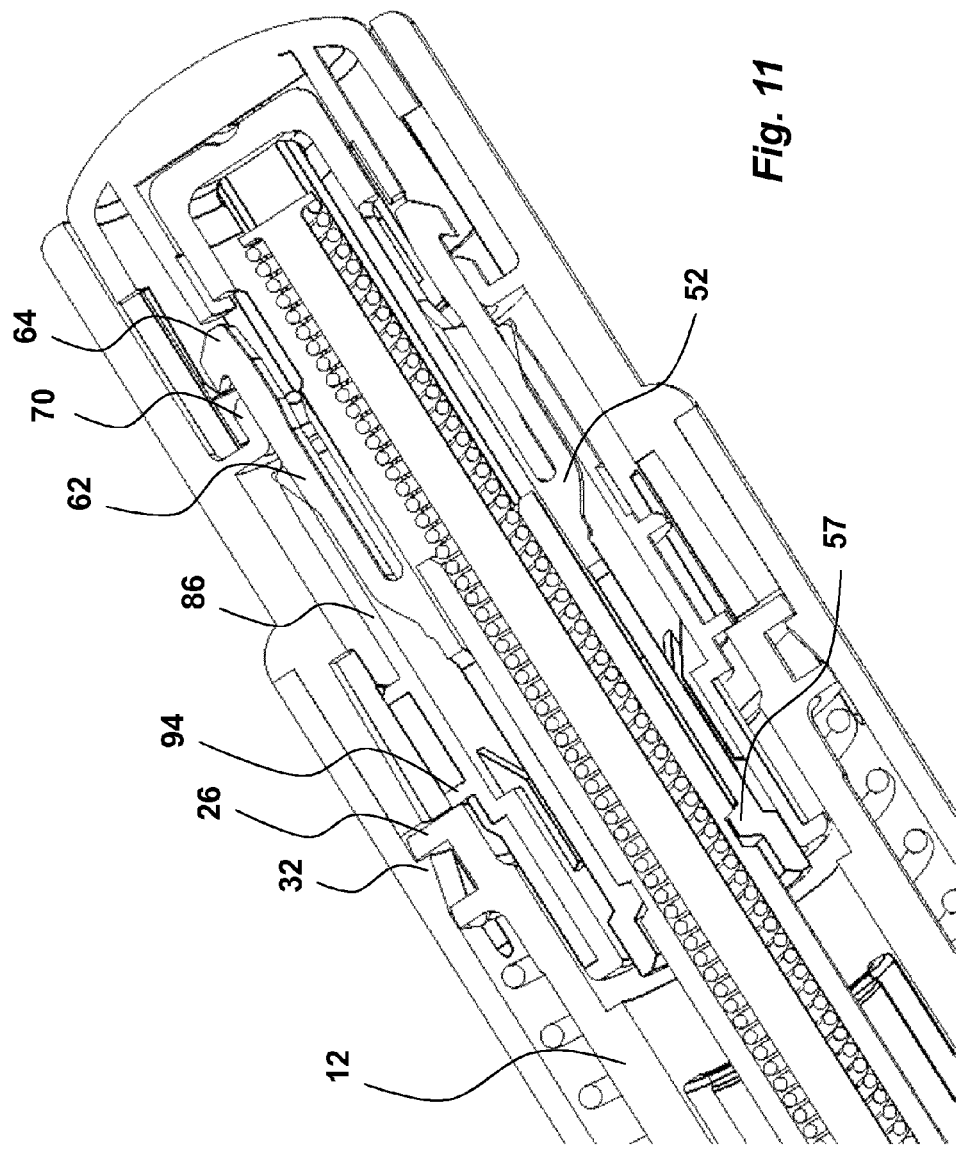
Figure 12:
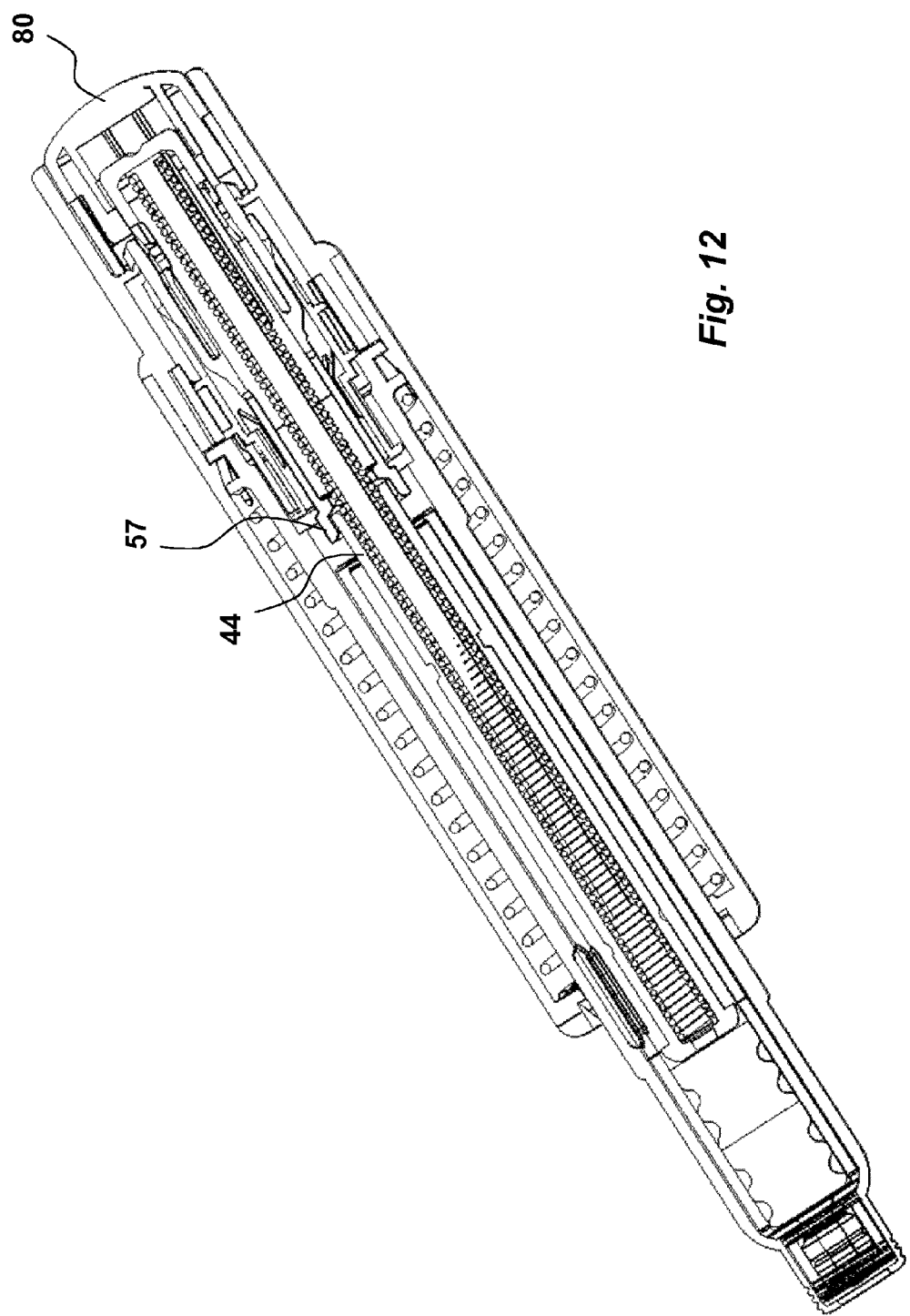
Figure 13:
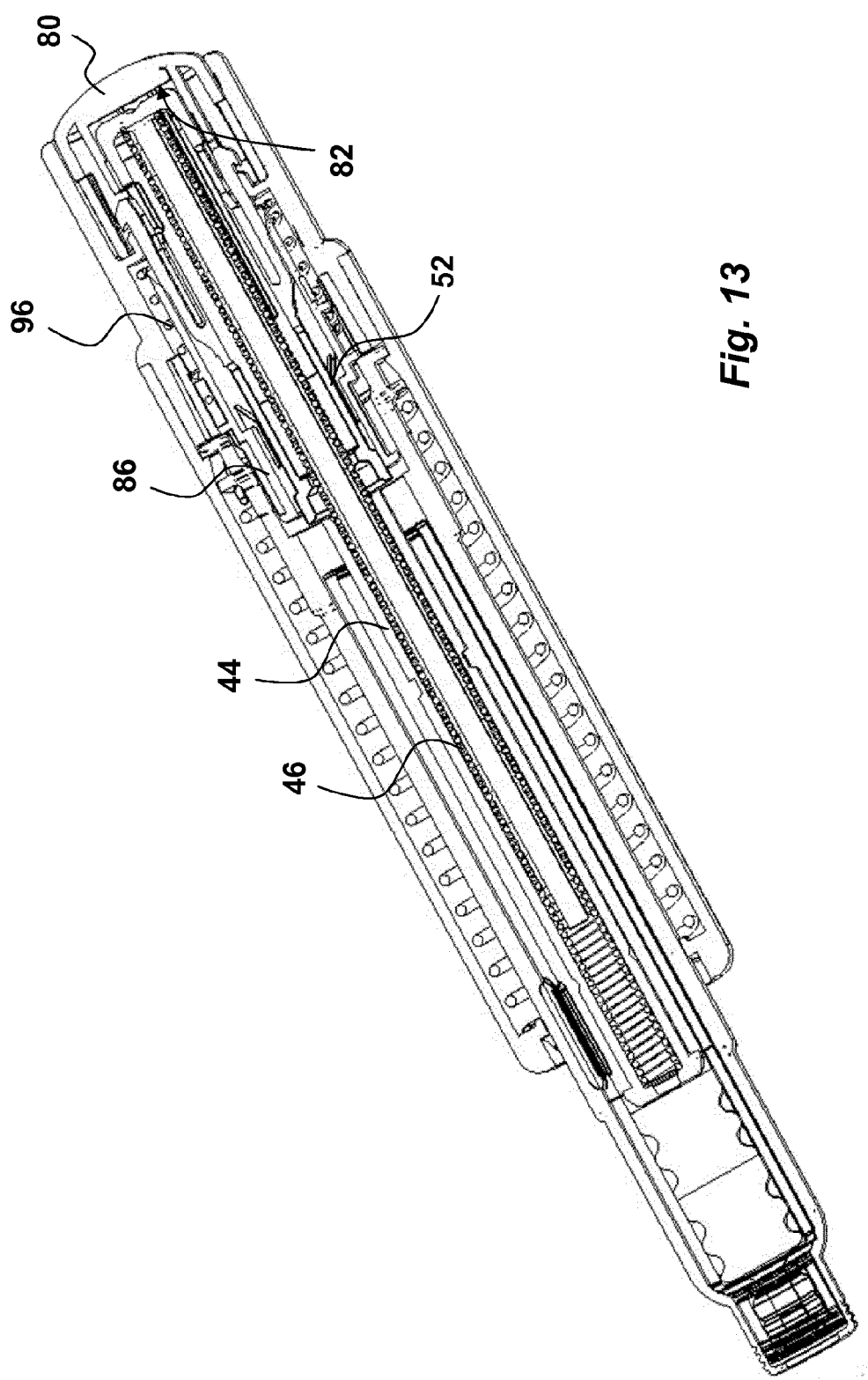

In the following detailed description of the invention, reference will be made to the accompanying drawings, of which FIG. 1 is a perspective view of a medicament delivery device according to the invention, FIG. 2 is an exploded view of the medicament delivery device according to FIG. 1, FIG. 3 is a cross-sectional side view of the medicament delivery device according to FIG. 1 in an initial position, FIGS. 4-9 are detailed views of components comprised in the medicament delivery device according to FIG. 1, FIG. 10 is a cross-sectional side view of the medicament delivery device according to FIG. 1 when mixing has been performed, FIG. 11 is a cross-sectional vie of a distal part of the medicament delivery device according to FIG. 1, when mixing has been performed, FIG. 12 is a cross-sectional side view of the medicament delivery device according to FIG. 1 when the injection sequence has been finished, and FIG. 13 is a cross-sectional side view of the medicament delivery device according to FIG. 1 when the injection sequence has been finished and indication information has been produced to a user.

DETAILED DESCRIPTION OF THE INVENTION

The present invention relates to a medicament delivery device, and more particularly to an injection delivery device comprising a housing formed by a distal housing part 10 and a proximal housing part 12, and wherein the distal housing part comprises a first distal housing part 10a and a second distal housing part 10b. It is however to be understood that other designs are feasible within the present invention. Further, said proximal housing part is arranged to accommodate a multi-compartment medicament container 34. The proximal and distal housing parts are generally tubular and arranged such that one housing part may move inside the other housing part. According to the present invention, said housing parts are designed and arranged to be movable in relation to each other from a first position in which said housing parts are partially extended in relation to each other, to a second position in which said housing parts are partially retracted in relation to each other. More particularly, the distal housing part is arranged with a proximally directed opening 14, FIG. 4, of a generally circular shape, through which opening the proximal housing part 12 extends, as seen in FIGS. 1 and 3. The device also comprises a drive mechanism arranged in said distal housing part 10 and said drive mechanism comprises a plunger rod 44.

The device further comprises an auto mixing mechanism configured to hold said housing parts in the first position and to lock said housing parts in the second position. The auto mixing mechanism comprises a mixing force member 30 operably arranged between said housing parts, such that a manual activation of said auto mixing mechanism allows said mixing force member 30 to cause the two housing parts to move from the first position to the second position whereby said plunger rod 44 acts on said multi-chamber medicament container 34 to perform a mixing of a medicament contained in said multi-compartment medicament container 34. The mixing force member 30 is arranged in a tensioned state when the housing parts are in said first position. The auto mixing mechanism further comprises mechanical inter-locking members interacting between the two housing parts. The mechanical inter-locking members are configured to releasably hold said housings in the first position against the force exerted by the mixing force member and to lock said housing parts in relation to each other after reaching the second position. Further, the mechanical inter-locking members are arranged such that an operational relative movement of said housing parts in a non-longitudinal direction of said device causes a release of said mixing force member from the tensioned state.

The mechanical inter-locking members comprise at least one first ledge 16 on a surface of one housing part and at least one first protrusion 22 on a surface of the other housing part. The at least one first ledge 16 comprises a seat 20, into which seat 20 said at least one first protrusion 22 fits, such that when said and at least one first protrusion 22 is positioned in said seat 20, the housing parts are releasably held in the first position. The mechanical inter-locking members further comprise at least one second protrusion 26 on a surface of one housing part and at least one generally wedge-shaped protrusion 32 or resilient tongue on a surface of the other housing part, such that when said at least one second protrusion 26 interacts with said at least one generally wedge-shaped protrusion 32 or resilient tongue, the housing parts are locked in the second position.

Figure 4:
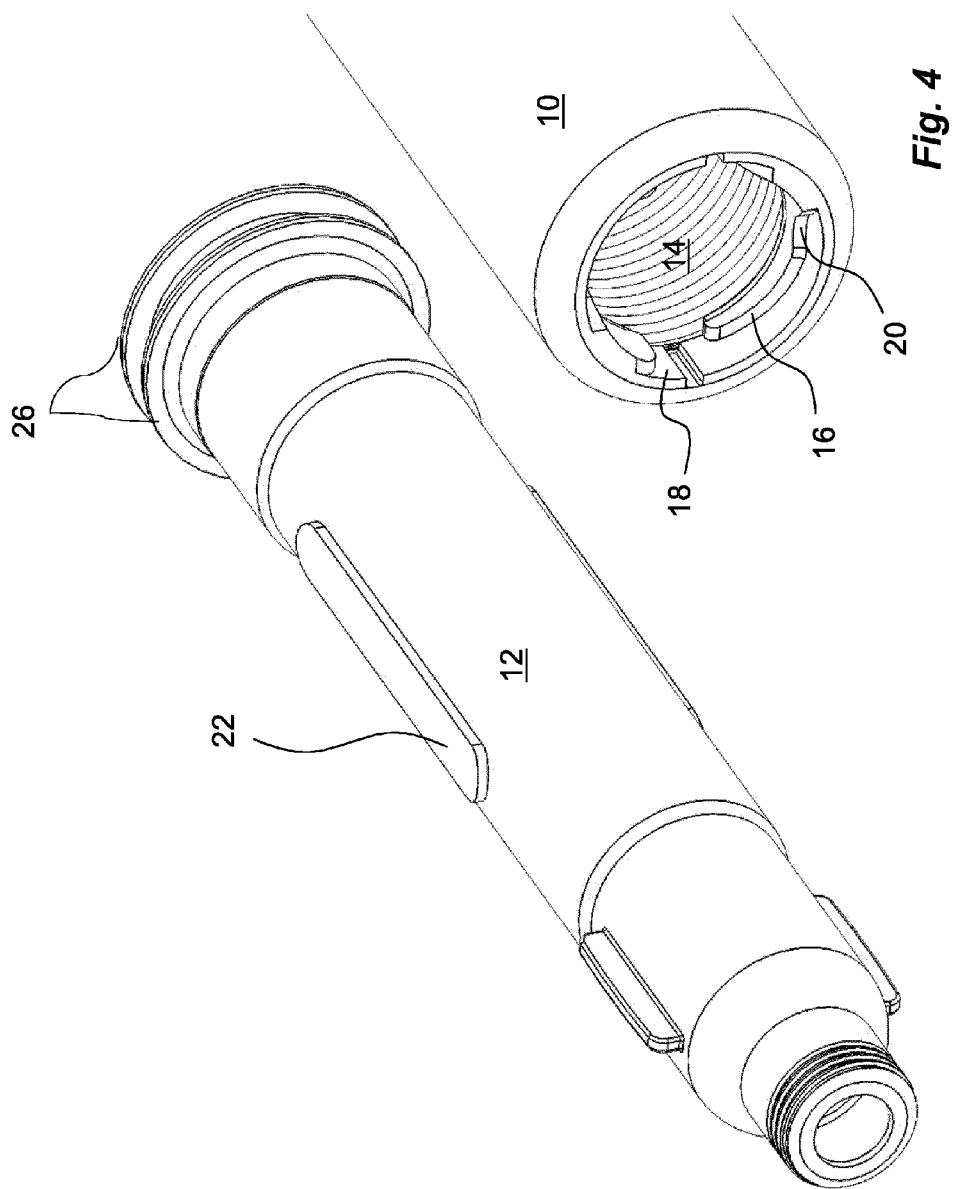

According to a preferred embodiment, the opening 14 of the distal housing part 10 is arranged with two ledges 16, FIG. 4, that extend circumferentially, where gaps 18 separate the ledges 16. Each ledge 16 is arranged with the cut-out or seat 20. The gaps 18 and the seats 20 are preferably positioned on opposite sides around the opening 14. The outer surface of the proximal housing part 12 comprises two first protrusions 22 in the form of longitudinally extending protrusions, wherein each distal end surface of said first protrusions 22 fits into respective seat 20, FIG. 4. Further, the distal end of the proximal housing part 12 is arranged with two second protrusions 26 in the form of two parallel circumferentially extending ledges, FIG. 4.

The mixing force member 30, in the embodiment shown is a compression spring, FIG. 3. Said mixing force member is arranged between a ledge 28 which extends circumferentially around the opening 14 of the distal housing part 10, and the proximally positioned second protrusion 26 of the proximal housing part 12.

Figure 5:
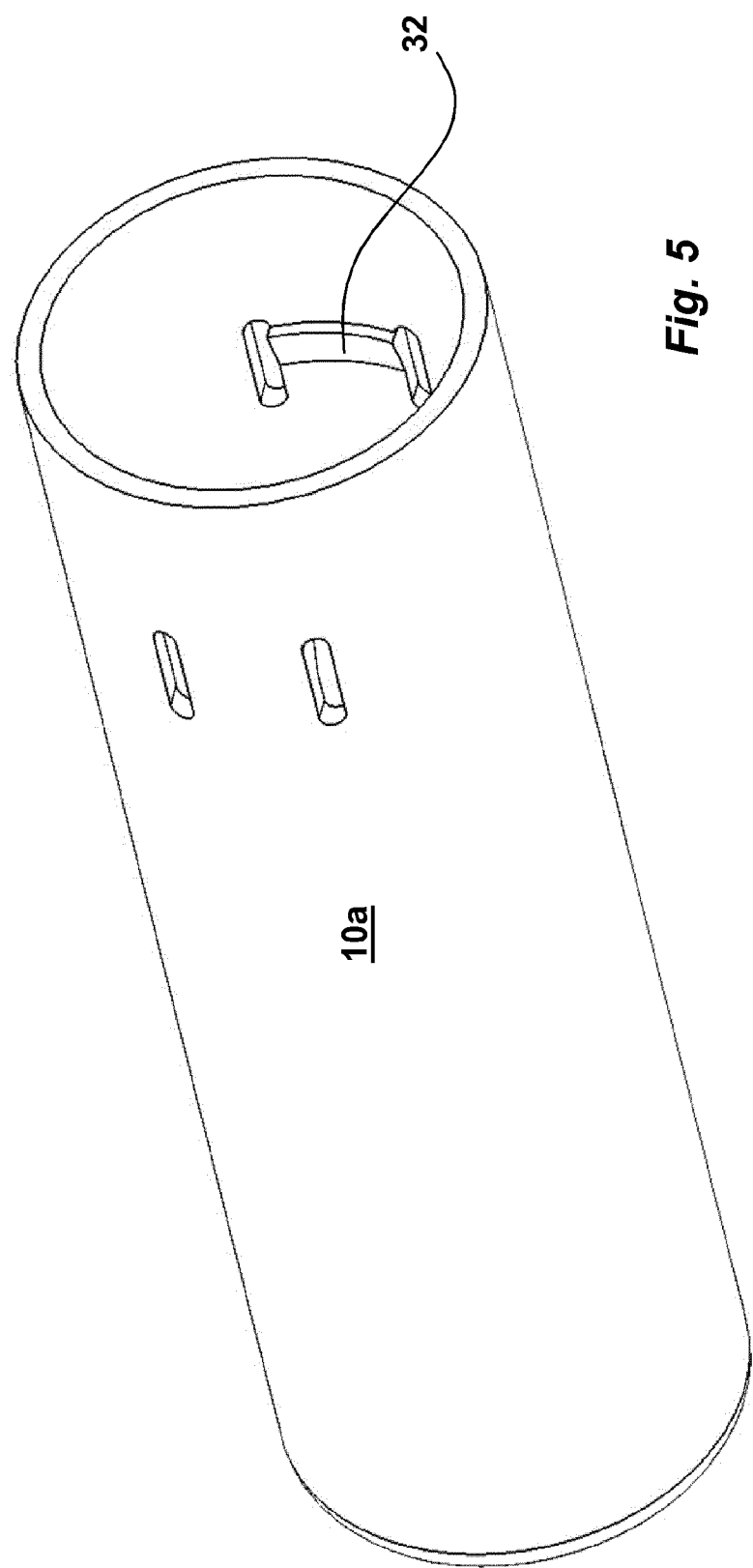

As seen in FIGS. 3 and 5, the generally wedge-shaped protrusions 32 on the inner surface of the distal area of the distal housing part 10 are intended to interact with the distally positioned second protrusions 26 of the proximal housing part 12, the function of which will be described below.

The proximal housing part 12 houses the multi-chamber container 34, FIGS. 2 and 3, wherein a proximal portion 36 of the multi-chamber container 34 fits into a proximal end portion 38 of the proximal housing part 12. Said proximal end portion 38 of the proximal housing part 12 has attaching means, e.g. threads on its outer circumferential surface, for allowing a delivery member e.g. a pen needle, such as a safety pen needle to be attached. The multi-chamber container 34 comprises at least two medicament substances arranged in each chamber, a distal stopper 40, a proximal stopper 42, FIG. 2, and redirecting passages between the chambers.

The plunger rod 44, FIGS. 2 and 3, is arranged to act on the distal stopper 40. The plunger rod 44 is formed as a tubular member with an outer diameter somewhat smaller than the inner diameter of the multi-chamber container 34 to be used.

The drive mechanism further comprises:
- a push button 80 protruding from said distal housing part and being interactively connected to the plunger rod;
- an activation member 52 comprising tubular flexible locking means 56 releasably connected to said plunger rod;
- drive force means 46 pre-tensioned arranged between a distal end surface 50 of the activation member and a proximal end wall 48 of the plunger rod;
- a locking member 86 coaxially arranged around said activation member 52 and being distally slidable in relation to said activation member 52 by said proximal housing part, between a holding position wherein said locking member 86 completely covers said tubular flexible locking means 56 holding said plunger rod 44 and thereby said drive force means 46 in a pre-tensioned state, and a releasing position wherein said locking member 86 only partially covers said flexible locking means 56.

In the embodiment shown, the drive force means 46 is a compression spring that is positioned inside the tubular plunger rod 44 with a proximal end abutting the proximal end wall 48, FIG. 3, of the plunger rod 44 and with a distal end abutting the distal end surface 50 of an activation member 52, FIGS. 2 and 3. Further, inside the drive force means 46, a guide rod 54 is arranged. The guide rod 54 extends through the proximal end wall 48 of the plunger rod with a distance A, the function of which will be explained below.

Figure 6:
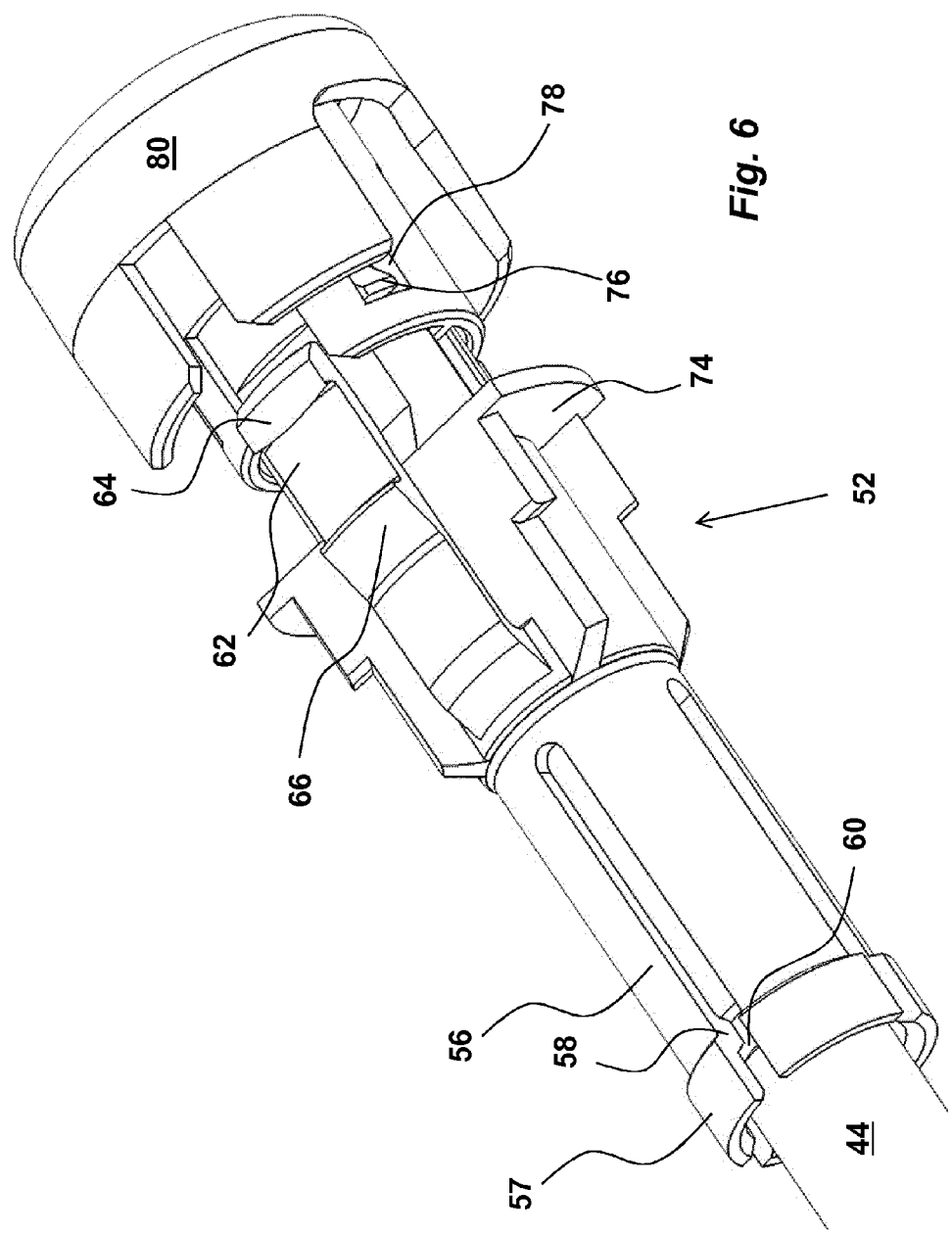

The activation member 52, FIG. 6, has a mainly tubular shape and is arranged surrounding the plunger rod 44. The tubular flexible locking means 56 of the activation member 52 are formed ad flexible tongues. Each tongue is arranged with an outwardly directed band-shaped part 57 with enlarged diameter as well as an inwardly directed ledge 58. Each inwardly directed ledge 58 is arranged with a shape as to fit into a circumferential groove 60 of the plunger rod 44, FIG. 6. The activation member 52 is further provided with flexible hook means 62 so as to form at least one flexible tongue having a radial outwardly directed hook 64 at its outer distal end, which hook means 62 is arranged with an inclined surface 66.

Figure 7:
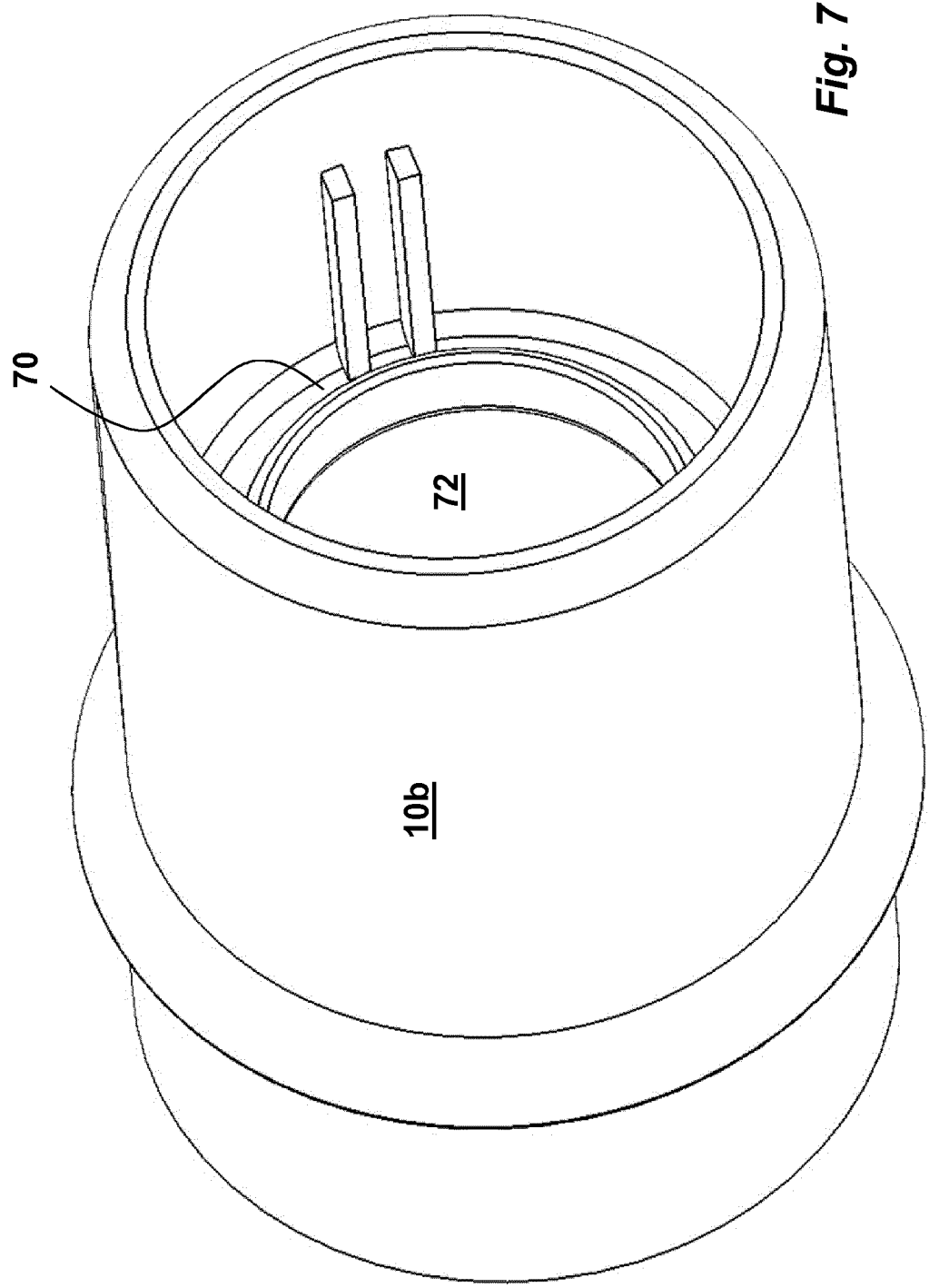

The flexible hook means 62, and the outwardly directed hooks 64 in particular, are arranged to interact with annular holding means 70 formed as a distally directed ledge arranged around a central passage 72 on a transversal wall surface of the distal housing part 10, FIG. 7, for preventing said push button 80 to be proximally displaced before said locking member 86 is moved from the holding position to the releasing position in order to avoid premature activation of the device.

Further, the activation member 52 also comprises at least two oppositely arranged stop ledges 74 directed radially outwards from the outer surface, on either side, FIG. 6. The activation member 52 is also provided with at least one radially outward-directed, wedge-shaped protrusion 76 interacting with at least one longitudinally extending slot 78 arranged in a tubular body part of a push button 80, such that the activation member 52 is longitudinally movable in relation to said push button 80.

The push button 80 is arranged with an inner surface 82, FIG. 3, located at a second predetermined distance "B" from the distal end surface 50 of the activation member 52, as seen in FIG. 3. The push button 80 is further arranged with at least two first proximally extending tongues 84, FIG. 2, wherein each tongue 84 has a proximally directed surface abutting a distal annular surface of the plunger rod 44 as seen in FIG. 8.

The locking member 86, FIG. 9, being of a generally tubular form comprises at its distal end at least two oppositely arranged cut-outs 88 of a generally rectangular shape forming at least two distally extending tongues 90, and wherein the widths of said cut-outs correspond to the width of the stop ledges 74 of the activation member 52. The locking member 86 also comprises a proximal end having a distal annular ledge 92 and a proximal annular ledge 94 on its outer surface.

The drive mechanism further comprises a resilient member 96 being a compression spring arranged between the at least two oppositely arranged stop ledges 74 of the activation member 52 and the distal annular ledge 92 of the locking member. The at least two distally extending tongues 90 of the locking member 86 are arranged to come in contact with the flexible hook means 62, and with the inclined surface 66 in particular, when the locking member 86 is displaced from the holding position to the releasing position, whereby the flexible hook means 62 are moved inwards and are free to by-pass the annular holding means 70.

The function of the device according to the invention will now be described.

The device will be delivered to the user as shown in FIGS. 1 and 3, where the multi-chamber medicament container 34 is placed in the proximal housing part 12 and the distal housing part 10 is attached to the proximal housing part 12. The housing parts are in the first position relative to each other, wherein the first protrusions 22 on the proximal housing part 12 are positioned in the seats 20 of the ledges 16, the mixing force member 30 is in a tensioned state between the ledge 28 of the distal housing part 10, and the proximal ledge 24 on the proximal housing part 12, as seen in FIG. 3.

The tubular flexible locking means 56 are engaged to the plunger rod 44 through the generally radial, inwardly directed ledges 58 fitting into the groove 60 of the plunger rod 44, FIG. 8. The locking member 86 is coaxially arranged around said activation member 52 in the holding position wherein said locking member 86 completely covers said tubular flexible locking means 56 holding said plunger rod 44 and thereby said drive force means 46 in the pre-tensioned state.

When a mixing is to be performed, the proximal housing part 12 is turned in relation to the distal housing part 10. The first protrusions 22 of the proximal housing part 12 will be moved out of the seats 20 and will slide along the ledges 16 until they are aligned with the gaps 18. The proximal housing part 12 is now free to move in relation to the distal housing part 10 towards the distal direction by the force of the mixing force member 30. Because the plunger rod 44 and the guide rod 54 are stationary, the movement of the proximal housing part, and thus the multi-chamber medicament container 34, in the distal direction will cause the medicament container 34 to move distally with respect to the plunger rod and the distal stopper 40 such that the redirecting passage is opened between the chambers and the medicament substances inside said multi-chamber container will be mixed, see FIG. 10.

The housing parts are now in the second position relative to each other, wherein the distal circumferential ledge 26 on the outer surface of the proximal housing part 12 has moved past the wedge-shaped protrusions 32, whereby the proximal housing part 12 is locked in relation to the distal housing part 10. At the same time the annular distal end part of the proximal housing part 12 abuts the proximal annular ledge 94 of the locking member 86 and forces said locking member 86 axially towards the distal end of the device against a force of the resilient member 96. The resilient member 96 is then tensioned. A proximal portion of the band-shaped part 57 is then partially situated outside the proximal annular end of the locking member 86, as seen in FIG. 11. The at least two distally extending tongues 90 of the locking member 86 will then come into contact with the inclined surface 66 of the protrusion of the hook means 62 on the activation member 52 whereby the hooks 64 are moved radially inwards.

The next step is to connect a delivery member as a needle or a safety pen needle to threaded neck 38 of the proximal housing part 12, and to apply the delivery member to the delivery site, i.e. to perform a manual penetration of the needle at an injection site, e.g. through the skin of a patient.

When activating the device, the user merely depresses the push button 80, FIG. 12, whereby the at least two first proximally extending tongues 84 of the push button 80 which are abutting the distal annular surface of the plunger rod 44, forces the plunger rod 44 to be moved towards the proximal end of the device. Since the plunger rod 44 is connected to the activation member 52 by the generally radial, inwardly directed ledges 58 fitting into the groove 60 of the plunger rod 44, the activation member 52 is also forced towards the proximal end of the device, and since the distal end of the guide rod 54 is abutting the distal end surface 50 of the activation member 52, the guide rod 54 is also forced towards the proximal end of the device, forcing the distal stopper 40 towards the proximal end of the device.

During the proximal displacement of the activation member, the hooks 64 by-pass the annular holding means 70 which is formed as a distally directed surface of a ledge arranged on the inner circumferential surface of the first distal housing part 10b, and the band-shaped part 57 completely emerges outside the proximal annular end of the locking member 86. The resilient properties of the tubular flexible locking means 56 of the activation member 52 force the band shaped part 57 to flex radially outwards, causing the ledges 58 to come out of the groove 60 of the plunger rod 44, which is then free to move under the force of the pre-tensioned drive force means 46 inside the plunger rod 44. The force of the drive force means 46 urges the plunger rod 44 first to be proximally displaced the distance A such that the proximal end wall of the plunger rod hits the distal stopper producing an audible and tactile indication. Then, further proximal displacement of the plunger rod also displaces the two stoppers in the proximal direction, whereby the mixed liquid substance of medicament is delivered, i.e. injected into the patient tissue, until the proximal stopper reaches the inner proximal end of the container, as seen in FIG. 12.

Just before the proximal stopper reaches the inner proximal end of the container, the distal annular surface of the plunger rod 44 passes the proximal annular surface of the tubular flexible locking means 56. The tubular flexible locking means 56 will then flex inwards and the activation member 52 will be forced in the distal direction inside the locking member 86 due to a remaining force on the drive force means 46 forcing the activation member 52 to move distally the second predetermined distance B such that the distal end surface 50 of the activation member 52 hits the inner surface of the transversal wall 82 of the push button 80, FIG. 13, producing an audible and tactile indication that the injection is finished. The medicament delivery device may now be safely removed from the injection site and discarded in a safe way.

It is to be understood that the embodiment described above and shown in the drawings is to be regarded as a non-limiting example of the invention and that it is defined be the patent claims.

The invention claimed is:

1. A medicament delivery device, comprising:
a distal housing part;
a proximal housing part configured to accommodate a multi-compartment medicament container, wherein the distal and proximal housing parts are movable in relation to each other from a first position, in which the distal and proximal housing parts are partially extended in relation to each other, to a second position, in which the distal and proximal housing parts are partially retracted in relation to each other;
a drive mechanism in the distal housing part, the drive mechanism comprising a plunger rod; and
an auto mixing mechanism configured to hold the distal and proximal housing parts in the first position and to lock the distal and proximal housing parts in the second position, wherein the auto mixing mechanism comprises mechanical inter-locking members arranged on the distal and proximal housing parts and a mixing force member having a spring operably arranged between the distal and proximal housing parts such that manual activation of the auto mixing mechanism releases the mechanical interlocking members, whereby the spring causes the distal and proximal housing parts to move from the first position, in which the spring is tensioned, to the second position, whereby the plunger rod acts on the multi-compartment medicament container to mix a medicament contained in the multi-compartment medicament container;
wherein the mechanical inter-locking members are arranged such that manual activation of the auto mixing mechanism includes relative movement of the distal and proximal housing parts, thereby releasing the mixing force member from the tensioned state; and the mechanical inter-locking members comprise at least one protrusion on a surface of one of the distal and proximal housing parts and at least one generally wedge-shaped protrusion or resilient tongue on a surface of the other of the distal and proximal housing parts, such that when the at least one protrusion interacts with the at least one generally wedge-shaped protrusion or resilient tongue, the distal and proximal housing parts are locked in the second position.

2. The device of claim 1, wherein the mechanical inter-locking members comprise at least one first ledge on a surface of one of the distal and proximal housing parts and another at least one protrusion on a surface of the other of the distal and proximal housing parts.

3. The device of claim 2, wherein the at least one first ledge comprises a seat, into which seat the another at least one protrusion fits, such that when the another at least one protrusion is positioned in the seat, the distal and proximal housing parts are releasably held in the first position.

4. The device of claim 1, wherein the distal and proximal housing parts are generally tubular and arranged such that one of the distal and proximal housing parts is movable inside the other of the distal and proximal housing parts.

5. The device of claim 1, wherein the device is an injection device.

6. The device of claim 5, wherein the injection device is an auto-injector.

7. A medicament delivery device, comprising:
a distal housing part;
a proximal housing part configured to accommodate a multi-compartment medicament container, wherein the distal and proximal housing parts are movable in relation to each other from a first position, in which the distal and proximal housing parts are partially extended in relation to each other, to a second position, in which the distal and proximal housing parts are partially retracted in relation to each other;
a drive mechanism in the distal housing part, the drive mechanism comprising a plunger rod; and
an auto mixing mechanism configured to hold the distal and proximal housing parts in the first position and to lock the distal and proximal housing parts in the second position, wherein the auto mixing mechanism comprises mechanical inter-locking members arranged on the distal and proximal housing parts and a mixing force member having a spring operably arranged between the distal and proximal housing parts such that manual activation of the auto mixing mechanism releases the mechanical interlocking members, whereby the spring causes the distal and proximal housing parts to move from the first position, in which the spring is tensioned, to the second position, whereby the plunger rod acts on the multi-compartment medicament container to mix a medicament contained in the multi-compartment medicament container;
wherein the mechanical inter-locking members are arranged such that manual activation of the auto mixing mechanism includes relative movement of the distal and proximal housing parts, thereby releasing the mixing force member from the tensioned state; the mechanical inter-locking members comprise at least one first ledge on a surface of one of the distal and proximal housing parts and at least one first protrusion on a surface of the other of the distal and proximal housing parts; the at least one first ledge comprises a seat, into which seat the at least one first protrusion fits, such that when the at least one first protrusion is positioned in the seat, the distal and proximal housing parts are releasably held in the first position; and the mechanical inter-locking members comprise at least one second protrusion on a surface of one of the distal and proximal housing parts and at least one generally wedge-shaped protrusion or resilient tongue on a surface of the other of the distal and proximal housing parts, such that when the at least one second protrusion interacts with the at least one generally wedge-shaped protrusion or resilient tongue, the distal and proximal housing parts are locked in the second position.

8. A medicament delivery device, comprising:
a distal housing part;
a proximal housing part configured to accommodate a multi-compartment medicament container, wherein the distal and proximal housing parts are movable in relation to each other from a first position, in which the distal and proximal housing parts are partially extended in relation to each other, to a second position, in which the distal and proximal housing parts are partially retracted in relation to each other;
a drive mechanism in the distal housing part, the drive mechanism comprising a plunger rod; and
an auto mixing mechanism configured to hold the distal and proximal housing parts in the first position and to lock the distal and proximal housing parts in the second position, wherein the auto mixing mechanism comprises mechanical inter-locking members arranged on the distal and proximal housing parts and a mixing force member having a spring operably arranged between the distal and proximal housing parts such that manual activation of the auto mixing mechanism releases the mechanical interlocking members, whereby the spring causes the distal and proximal housing parts to move from the first position, in which the spring is tensioned, to the second position, whereby the plunger rod acts on the multi-compartment medicament container to mix a medicament contained in the multi-compartment medicament container;
wherein the drive mechanism further comprises:
a push button that protrudes from the distal housing part and is operatively connected to the plunger rod;
an activation member, comprising a tubular flexible lock that is releasably connected to the plunger rod;
a driver pre-tensionedly arranged between a distal end surface of the activation member and a proximal end wall of the plunger rod;
a locking member coaxially arranged around the activation member and distally slidable in relation to the activation member by the proximal housing part between a holding position, in which the locking member completely covers the tubular flexible lock, holding the plunger rod and the driver in a pre-tensioned state, and a releasing position, in which the locking member partially covers the tubular flexible lock.

9. The device of claim 8, wherein the activation member further comprises at least one flexible hook that interacts with an annular holding device arranged on an inner circumferential surface of the distal housing part for preventing the push button from being proximally displaced before the locking member moves from the holding position to the releasing position, thereby preventing premature activation of the device.

10. The device of claim 9, wherein the locking member comprises at least two distally extending tongues arranged to contact the at least one flexible hook when the locking member is displaced from the holding position to the releasing position, whereby the at least one flexible hook is moved inward and is able to bypass the annular holding device.

11. The device of claim 10, wherein the push button comprises at least two first proximally extending tongues, each of which has a proximally directed surface abutting a distal annular surface of the plunger rod.

12. The device of claim 11, wherein the tubular flexible lock comprises generally radial, inwardly directed ledges, and the plunger rod comprises a circumferential groove shaped to fit the ledges.

* * * * *